United States Patent [19]

Toya et al.

[11] Patent Number: 4,923,449
[45] Date of Patent: May 8, 1990

[54] APPARATUS FOR COLLECTING CONSTANT AMOUNTS OF BLOOD FROM INDIVIDUAL DONORS

[75] Inventors: Matsumi Toya, Koushoku; Yasuyuki Miyairi, Nagano, both of Japan

[73] Assignees: Kabushiki Kaisha Tiyoda Seisakusho, Nagano; Kawasumi Kagaku Kogyo Kabushiki Kaisha, Tokyo, both of Japan

[21] Appl. No.: 122,025

[22] Filed: Nov. 18, 1987

[30] Foreign Application Priority Data

Nov. 19, 1986 [JP] Japan .................... 61-176584
Mar. 30, 1987 [JP] Japan .................... 62-74240

[51] Int. Cl.⁵ .................................. A61M 5/005
[52] U.S. Cl. .................................. 604/245; 604/403
[58] Field of Search ........ 604/245, 903, 317, 408–410, 604/65, 67, 73

[56] References Cited

U.S. PATENT DOCUMENTS

| | | | |
|---|---|---|---|
| 2,647,514 | 8/1953 | Ellis | 604/903 |
| 2,845,929 | 8/1958 | Strumia | 604/903 |
| 2,982,286 | 5/1961 | Welch Jr. | 604/245 |
| 3,557,789 | 1/1971 | Poitras | 604/245 |
| 3,583,400 | 6/1971 | Memhardt | 604/245 |
| 3,633,566 | 1/1972 | Grabhorn | 604/903 |
| 3,698,494 | 10/1972 | Gaudin | 604/245 |
| 3,924,700 | 12/1975 | Lindsey et al. | 604/245 |
| 3,960,224 | 6/1976 | Silvers | 604/245 |
| 4,095,658 | 6/1978 | Kendall et al. | 604/245 |
| 4,267,837 | 5/1981 | Purdy et al. | 604/245 |

Primary Examiner—John D. Yasko
Assistant Examiner—Kathleen A. Daley
Attorney, Agent, or Firm—Ladas & Parry

[57] ABSTRACT

An apparatus for the collection of blood via a collapsible inflow pipe into an inflatable bag having an anticoagulant prefilled therein. The bag is placed on a weighing platform coupled to a load cell, which produces an electric voltage signal representative of the weight of the blood being collected in the bag. The load cell is mounted on a swing cradle capable of oscillation about a horizontal axis, so that the bag is shaken during blood collection for intimately intermingling the collected blood and the anticoagulant. When a predetermined amount of blood is collected, as ascertained from the voltage output of the load cell, a controller actuates a collection stop mechanism thereby causing the same to tightly grip and collapse the inflow pipe.

8 Claims, 7 Drawing Sheets

APPARATUS FOR COLLECTING CONSTANT AMOUNTS OF BLOOD FROM INDIVIDUAL DONORS

BACKGROUND OF THE INVENTION

This invention relates to apparatus for collection of blood as a therapeutic agent, and more specifically to such apparatus featuring provisions for collection of prescribed amounts of blood from individual donors with little or no human assistance. The apparatus in accordance with the invention lends itself to use at blood banks, hospitals, blood donation cars, and any other institutions or agencies where blood is donated for transfusion and other purposes.

Efficient collection of blood from as many donors as possible is a key factor for the extensive practice of transfusions and related methods of therapy at numerous medical organizations existing today. The usual practice for blood collection involves the use of a disposable bag, fabricated from polyvinyl chloride in sheet form, for each single donor. The bag has a pipe of pliant material extending therefrom and terminating in an intravenous needle. An adequate amount of anticoagulant is previously introduced into the bag in order to prevent the clotting of the collected blood.

In the use of the collection bag the needle is thrusted into a vessel of the donor, with the result that the blood flows through the pipe into the bag by virtue of the blood pressure of the donor himself. Before the collection the donor can choose the amount of blood he will donate at one time from between 200 cubic centimeters (cc) and 400 cc, although, of course, these values may vary from country to country. A collection bag having a capacity matching each donor's choice is used for collection. In the applicant's country, law permits collection errors up to +10 percent of the amount chosen by the donor, there being no regulation against shortages.

Thus, for the collection of the required amount of blood within the tolerance limit, a supervisor has usually had to attend to each donor throughout the course of donation. This has necessitated an expenditure of substantial energy. For it takes five to ten minutes, depending upon the donor's blood pressure and vessel size, to collect a preselected amount of blood from one donor by the above conventional method.

A more advanced collection system is found in Japanese Patent Publication (KOKOKU) No. 51-3153 published Jan. 31, 1976. This known system teaches the use of a hermetically enclosed space in which an inflatable collection bag is placed. As a partial vacuum is created in the enclosed space, a prescribed amount of blood is drawn from the donor's body into the bag more quickly than if the blood is fed solely by the blood pressure of the donor. This advantage is offset, however, by the difficulties arising for system makeready when different amounts of blood must be collected from successive donors. An additional weakness is that the amount of blood that has been collected is not readily apparent to the supervisor during the progress of donation.

It has also been suggested to measure the amount of collection by weight, rather than by capacity, as disclosed in Japanese Utility Model Publication (KOKOKU) No. 58-54090 dated Dec. 9, 1983. Being based on the principle of the spring balance, the apparatus according to this utility model is unsatisfactory in the accuracy with which the collected blood is weighed. The accuracy of weighing becomes even worse when, as is standard in the art, the bag is shaken during collection for the intimate intermingling of the collected blood and the anticoagulant.

The shaking of the bag requires the oscillation, rather than rectilinear reciprocation, of the platform on which the bag is mounted during collection. The accurate weighing of the collected blood on the pivoted oscillatory platform demands additional considerations that must go into the design of the apparatus.

SUMMARY OF THE INVENTION

The present invention ovecomes the listed weaknesses of the prior art and provides an improved apparatus capable of efficient, automatic collection of prescribed amounts of blood with a minimum of errors.

In summary the blood collection apparatus in accordance with the invention is intended for use with a collection bag unit having an inflatable bag to be filled with blood, a collapsible inflow pipe extending from and communicating with the bag for introducing the blood therein, and a needle at the tip of the inflow pipe for blood collection from a donor. The apparatus particularly features the use of a load cell coupled to a weighing platform on which the bag is placed during blood collection. The load cell puts out an electric weight signal representative of the weight of the blood being collected in the bag. The load cell together with the weighing platform is mounted to a swing cradle which is oscillated about a horizontal axis by a shaking mechanism for shaking the bag on the weighing platform. Responsive to the weight signal from the load cell is a control means which puts out a collection stop signal when a preselected amount of blood is collected in the bag. The collection stop signal is applied to a collection stop mechanism for causing the same to terminate the blood collection by collapsing the inflow pipe of the bag unit.

The blood can be introduced via the inflow tube into the bag solely by virtue of the donor's blood pressure. However, for a higher rate of blood collection, the weighing platform may be disposed in a vacuum chamber, so that the blood may be fed by the differential between the blood pressure and the negative pressure created in the vacuum chamber.

The increasing weight of the blood in the bag is measured piezoelectrically by the load cell and is thereby converted into the electric weight signal. Usually, the specific gravity of each donor's blood is measured prior to collection, and the blood is collected only when the specific gravity is found to fall within a prescribed range. It is therefore possible to collect a predetermined amount of blood within the noted tolerance range through weight measurement. The weight signal from the load cell accurately represents the weight of the blood that has been collected, so that the blood collection can be terminated by the collection stop mechanism just when the preselected amount of blood is collected. If the bag has been placed in the evacuated chamber, this chamber may also be placed in communication with the atmosphere upon completion of the blood collection.

It should be appreciated that the amount of blood being collected is measured piezoelectrically in accordance with the invention, instead of by a spring balance or equivalent weighing machines as in the prior art. A particular advantage accruing from the use of the load cell is that it is far less affected than other types of weighing machines by the shaking of the bag during blood collection. This advantage becomes all the more pronounced because the shaking of the bag is unavoidable for intimately intermingling the collected blood and the anticoagulant that has been previously introduced into the bag.

The above and other features and advantages of this invention and the manner of realizing them will become more apparent, and the invention itself will best be understood, from a study of the following detailed description and appended claims with reference had to the attached drawings.

DETAILED DESCRIPTION OF THE INVENTION

Figure 1:
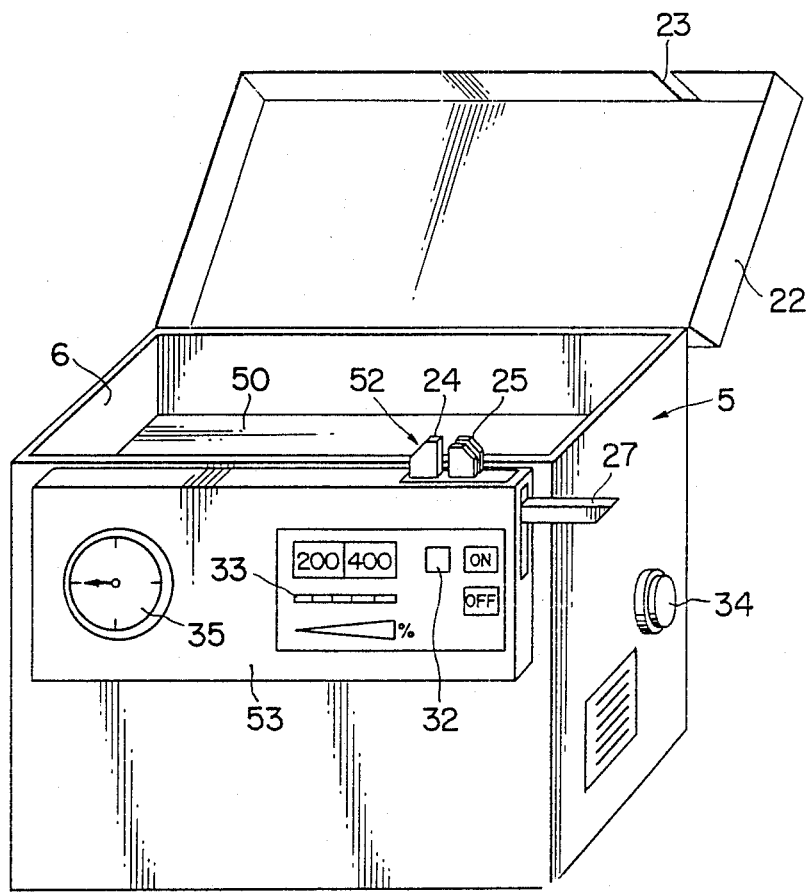
FIG. 1 is a perspective view of the blood collection apparatus constructed in accordance with the novel concepts of the invention.

As illustrated in its entirety in FIG. 1, the blood collection apparatus in accordance with the invention includes a generally boxlike, open-top enclosure 5 having a hinged lid 22 of rigid plastic material, preferably acrylic resin, for openably closing the top of the enclosure. Formed within the enclosure 5 and at a relatively short distance from the lid 22 is a horizontal partition 50 for defining an upwardly open vacuum chamber 6 which can be hermetically closed by the lid.

Figure 2:
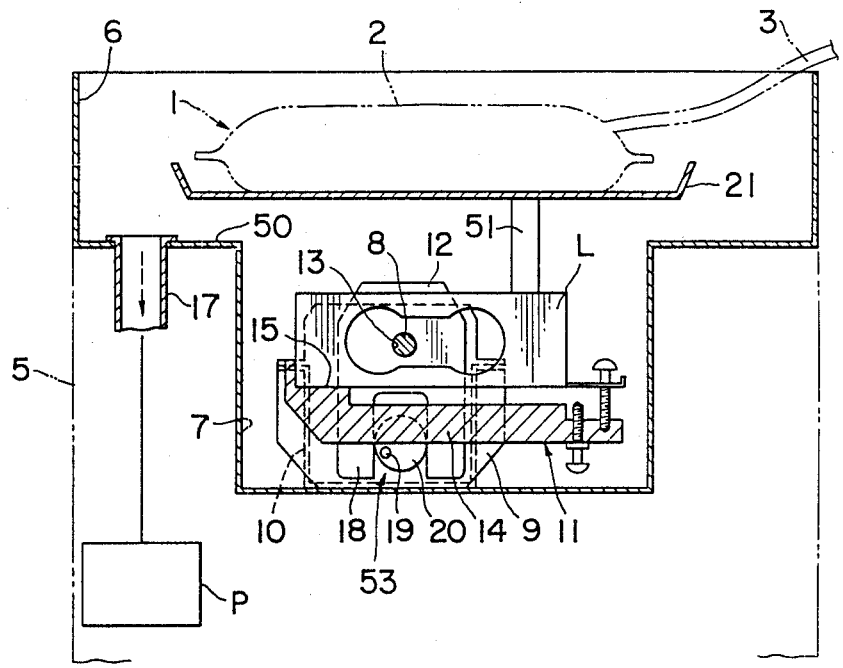
FIG. 2 is an enlarged fragmentary vertical section through the apparatus of FIG. 1, showing in particular the weighing platform, load cell, swing cradle, and bag shaking mechanism.

It will be observed from FIG. 2 that the vacuum chamber 6 accommodates a weighing platform 21 as well as a collection bag unit 1 placed thereon. The partition 50 is centrally depressed at 7 to provide a space, in open communication with the vacuum chamber 6, for receiving a load cell L coupled to the weighing platform 21 and means for shaking the platform during blood collection, as will be detailed presently.

Figure 6:
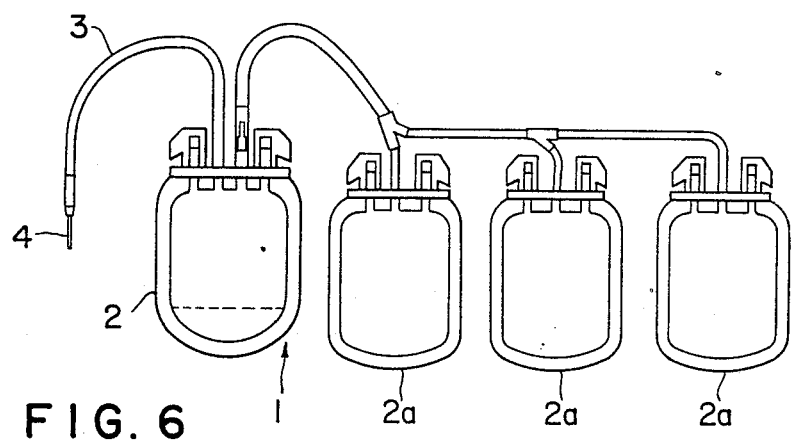
FIG. 6 is an illustration of a collection bag unit for use with the apparatus of FIG. 1.

As illustrated in detail in FIG. 6, the collection bag unit 1 can be of the conventional design comprising an inflatable bag 2 of pliant plastic sheet material such as, typically, polyvinyl chloride. A collapsible blood inflow pipe 3, which can be of the same material as the bag 2, extends therefrom and has an intravenous needle 4 attached to its tip. The bag 2 contains a suitable amount of anticoagulant introduced therein preparatory to use. One such collection bag unit 1 is used for each donor.

The illustrated collection bag unit 1 may be additionally provided with a supplementary bag or bags 2a which can be placed in and out of communication with the primary bag 2. The supplementary bag or bags are for use in separating the whole blood that has been collected in the primary bag 2, into such useful blood components as red corpuscles, plasma, white corpuscles, platelets, cryoprecipitates, etc. Up to three such supplementary bags may be combined with the primary bag 2 via suitable flexible piping to make up one collection bag unit. The primary and supplementary bags may be stacked up on the weighing platform 21 during blood collection.

Figure 4:
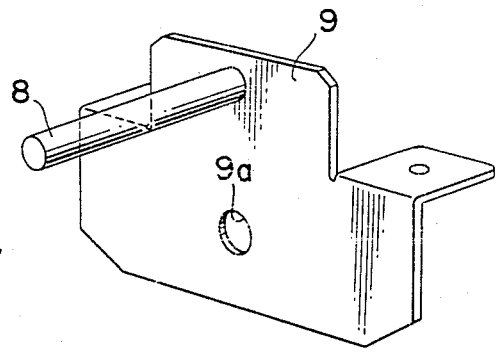
FIG. 4 is an enlarged perspective view of a support plate supporting a horizontal pivot pin about which the swing cradle of FIG. 2 oscillates.

With reference back to FIG. 2 an upstanding support plate 9 is secured to a fixed mounting lug 10 which is bottomed against the depression 7 in the partition 50. As will be seen also from FIG. 4, a horizontal pivot pin 8 is cantilevered to the support plate 9 for supporting a swing cradle 11. The load cell L is rigidly mounted on the swing cradle 11 for joint oscillation therewith about the horizontal pivot pin 8.

Figure 5:
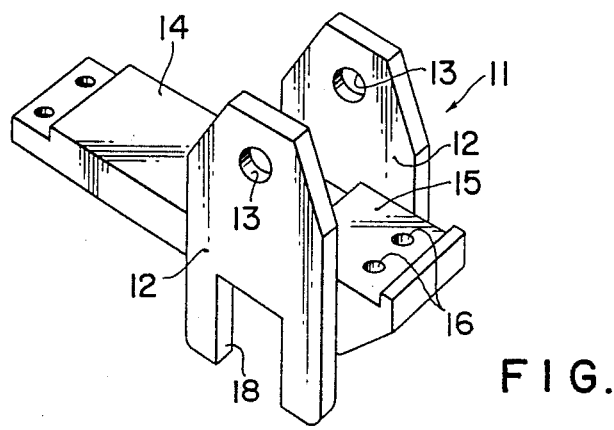
FIG. 5 is an enlarged perspective view of the swing cradle.

FIG. 5 is a detailed illustration of the swing cradle 11 on an enlarged scale. It comprises an elongate major portion 14 generally extending substantially horizontally, and a pair of upstanding lugs 12 secured to the opposite sides of the major portion and extending upwardly therefrom. A pair of aligned holes 13 are defined in the lugs 12 for rotatably receiving the pivot pin 8, so that the swing cradle 11 can oscillate about this pivot. The major portion 14 has a raised seat 15 formed adjacent one end thereof.

A reconsideration of FIG. 2 will reveal that the load cell L is mounted fast to the swing cradle 11 by having a proximal end portion thereof fastened to the raised seat 15 by screws, not shown, which are inserted into and through clearance holes 16 from the cradle underside. Extending from a distal end of the load cell L, an upstanding rod 51 is coupled to the weighing platform 21.

For oscillating the swing cradle 11 and hence for shaking the bag 2 of the collection bag unit 1 on the weighing platform 21 during blood collection, there is provided a bag shaking mechanism 53, FIG. 2, which acts directly on the swing cradle. It will be noted from both FIGS. 2 and 5 that one of the lugs 12 of the swing cradle 11 has a pair of cam follower arms 18 depending therefrom in parallel spaced relation to each other. The bag shaking mechanism 53 includes an eccentric cam 20 somewhat loosely engaged between the pair of cam follower arms 18. The eccentric cam 20 is eccentrically and rigidly mounted on the armature shaft 19 of an electric drive motor which is not seen in FIG. 2 but which is to appear in subsequent figures of the drawing attached hereto. The drive motor is mounted fast to the support plate 9, with the armature shaft 19 extending with clearance through a hole 9a, FIG. 4, in the support plate. Thus, as the drive motor is set into rotation, the eccentrically revolving cam 20 will act on the pair of cam follower arms 18 thereby causing the swing cradle 11 to swing about the pivot pin 8 and so shaking the bag 2 on the weighing platform 21.

It will also be noted from FIG. 2 that the vacuum chamber 6 as well as the space bounded by the depression 7 in the partition 50 communicates via a conduit 17 with a vacuum pump P on the bottom of the enclosure 5. An adjustable throttle valve, not shown, may be provided between vacuum chamber 6 and vacuum pump P for controlling the degree of vacuum in the vacuum chamber. As the lid 22 is hermetically closed against the enclosure 5, the vacuum chamber 6 can be evacuated by the vacuum pump P for drawing the blood from the donor into the bag 2 on the weighing platform 21. It is to be noted, however, that the evacuation of the chamber 6 is no essential feature of the invention, since blood can be collected as aforesaid solely by the blood pressure of the donor. Seen at 23 in FIG. 1 is a recess formed in the lid 22 to permit the inflow pipe 3 of the bag unit 1 to extend outwardly therethrough when the lid is closed.

Figure 7:
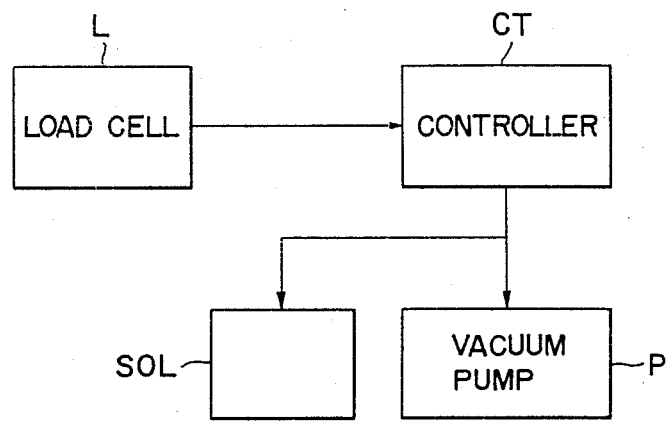
FIG. 7 is a block diagram of the electric control system incorporated with the apparatus of FIG. 1.

As is well known, the load cell L puts out an electric voltage signal proportional to the applied pressure, which in this case is the weight of the collected blood within the bag 2 on the weighing platform 21. The load cell L is electrically connected to a controller CT, shown both in FIGS. 7 and 8, for delivering thereto the electric weight signal representative of the weight of the collected blood. The controller CT is connected in turn to both the vacuum pump P and a solenoid SOL forming a part of a collection stop mechanism to be set forth subsequently. Inputting the weight signal from the load cell L, the controller CT ascertains the weight of the blood being collected in the bag 2 and puts out a collection stop signal for setting the vacuum pump P out of operation, and for energizing the solenoid SOL, when a preselected amount of blood is collected. Upon energization of the solenoid the collection stop mechanism will operate to terminate blood inflow into the bag 2 by collapsing the inflow pipe 3 at a point intermediate its opposite ends.

Figure 3:
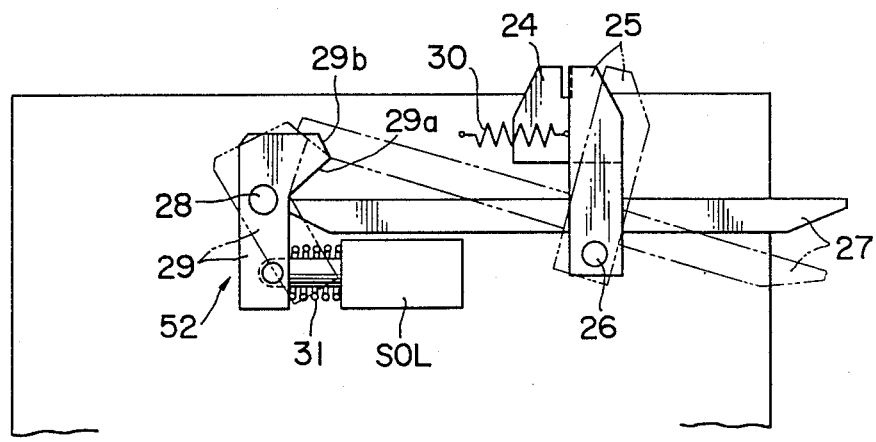
FIG. 3 is an enlarged side elevation of the collection stop mechanism included in the apparatus of FIG. 1.

Although FIG. 1 shows some parts of the collection stop mechanism, as generally indicated by the numeral 52, FIG. 3 better reveals its construction including the solenoid SOL. The collection stop mechanism 52 further comprises a fixed gripping jaw 24 and a movable gripping jaw 25, which are arranged to engage therebetween the blood inflow pipe 3 of the bag unit 1 as it extends out of the enclosure 5 through the recess 23 in the lid 22. Pivoted at 26 on the enclosure 5, the movable gripping jaw 25 is movable toward and away from the fixed gripping jaw 24. A helical tension spring 30 biases the movable gripping jaw 25 toward the fixed gripping jaw 24.

Rigidly coupled to the movable gripping jaw 25 and extending at right angles therewith is a hand lever 27 having its right hand end, as viewed in FIG. 3, extending outwardly from within the enclosure 5. The left hand end of the hand lever 27 is arranged for operative engagement with a locking lever 29 which is medially pivoted at 28 on the enclosure 5. One end of the locking lever 29 is coupled to the plunger of the solenoid SOL. When this solenoid is unenergized, a helical compression spring 31 sleeved upon its plunger holds the locking lever 29 in the position depicted by the solid lines in FIG. 3. With the locking lever 29 in this normal position, the hand lever 27 also lines in its solid line position as the movable gripping jaw 25 is urged against the fixed gripping jaw 24 by the force of the tension spring 30.

It will further be observed from FIG. 3 that the locking lever 29 has an angled slideway 29a and abutment 29b formed on its edge facing the hand lever 27. When the hand lever 27 is manually turned clockwise, as seen in FIG. 3, against the force of the tension spring 30, the left hand end of the hand lever will slide on the slideway 29a, turning the locking lever 29 counterclockwise against the force of the compression spring 31 in so doing, and will come to ride on the abutment 29b. Now the movable gripping jaw 25 is locked in its position away from the fixed gripping jaw 24. Upon subsequent energization of the solenoid SOL, the locking lever 29 will unlock the hand lever 27 thereby permitting the movable gripping jaw 25 to pivot toward the fixed gripping jaw 24 under the bias of the tension spring 30.

Seen at 32 in FIG. 1 is a switch button on a control panel 53 on the front face of the enclosure 5 for presetting the electric circuitry of the apparatus for either 200 cc or 400 cc blood collection. Also disposed on the control panel 53 is a row of five light-emitting diodes (LEDs) or like light sources. The LEDs 53 will glow one after another when every 20% of the preselected amount of blood is collected, so that all the LEDs will glow upon completion of the blood collection. A vacuum control knob 34 is disposed on the right hand side, as seen in FIG. 1, of the enclosure 5 for manually controlling the unshown throttle valve between vacuum chamber 6 and vacuum pump P. Observing a pressure gage 35 on the control panel 53, the operator may turn the knob 34 to control the degree of vacuum established in the vacuum chamber 6 and, in consequence, the rate of blood collection from each donor.

In the use of the blood collection apparatus constructed as in the foregoing, the bag 2 of an unused collection bag unit 1 is placed on the weighing platform 21, as indicated by the phantom outline in FIG. 2, after opening the lid 22. The inflow pipe 3 of the bag unit 1 is threaded between the pair of gripping jaws 24 and 25 of the collection stop mechanism 52. It is understood that the exposed right hand tip, as seen in FIGS. 1 and 3, of the hand lever 27 has been depressed against the force of the tension spring 50. As the left hand tip of the hand lever rides on the abutment 29b of the locking lever 29, the movable gripping jaw 25 is retained away from the fixed gripping jaw 24, so that the inflow pipe 3 can pass uncollapsed between these jaws.

The needle 4 at the tip of the inflow pipe 3 may now be inserted in a blood vessel of the donor. The blood will flow from the donor into the bag 1 solely under his own blood pressure. However, for a higher rate of blood collection, the vacuum chamber 6 may be evacuated, provided that the donor has been found to be capable of withstanding such rapid donation. Toward this end the lid 22 may be closed, and the vacuum pump P may be set into operation. Atmospheric air will be admitted into the vacuum chamber 6 only at a minimal rate as the inflow pipe 3 extends outwardly from the vacuum chamber 6 through the recess 23 in the bottom edge of the lid 22. Upon evacuation of the vacuum chamber 6 the blood will be drawn into the bag 2 by the differential between the negative pressure of that chamber and the donor's blood pressure. The resulting rate of collection will be higher than in the case where the blood is fed only by the blood pressure.

During such blood collection, either by the blood pressure only or by the evacuation of the chamber 6, the drive motor of the bag shaking mechanism 53 may be maintained in constant rotation. The eccentric cam 20 on the armature shaft of the motor will act on the pair of cam follower arms 18 of the swing cradle 11 thereby causing the latter to oscillate about the horizontal pivot 8 together with the load cell L, weighing platform 21 and bag 2. With the bag 2 so shaken, the anticoagulant that has been present therein will intimately mingle with the incoming blood for maintaining its fluid state.

Strained by the increasing weight of the blood within the bag 2, the load cell L will constantly deliver to the controller CT the weight signal representative of the weight of the collected blood. It has been stated that the specific gravity of each donor's blood is measured prior to collection, and the blood is collected only when its specific gravity is found to fall within a prescribed range. It is therefore possible to collect a prescribed amount of blood within the noted tolerance range through the measurement of weight instead of capacity.

It must be pointed out, however, that the bag 2, weighing platform 21 and load cell L are all in constant angular displacement during blood collection. Not only the angular position, but also the varying degrees of acceleration, of these members affect the measurement of the blood weight by the load cell. The resulting difference between the actual weight of the collected blood and the measurement of the load cell will be negligible, being normally up to three percent or so.

However, for more accurate measurement, the weight signal produced by the load cell L may be sampled periodically (e.g. every 12/1000 second), and the weight may be ascertained from these samples, at the controller CT. Alternatively, the weight signal may be sampled when the load cell L is in the same angular position, as will be later explained in more detail. Each cycle of oscillation of the swing cradle 11 is typically from two to three seconds, much shorter than the time required for blood collection from one donor. Therefore, such intermittent measurement will enable collection with a practically acceptable degree of accuracy.

Figure 8:
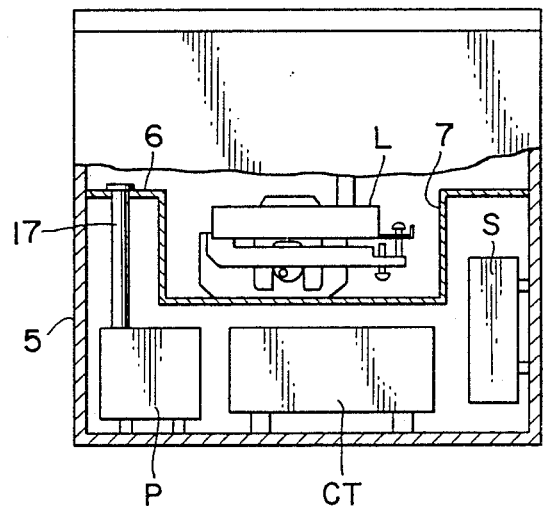
FIG. 8 is an elevation of the apparatus of FIG. 1, partly shown broken away to reveal those parts which are not shown in FIG. 2.

The LEDs 33 on the front face of the enclosure 5 will glow one after another with the increasing amount of blood within the bag 2, making possible the visual confirmation of the progress of collection. As desired, the controller CT may be adapted for audio-announcement of the progress and completion of collection. FIG. 8 shows at S the means for the production of such audio-announcements.

When a preselected amount (e.g. 200 cc or 400 cc) of blood is collected, the controller CT will produce, in response to the weight signal from the load cell L, the collections top signal for causing the energization of the solenoid SOL of the collection stop mechanism 52. The solenoid SOL on energization will turn the locking lever 29 counterclockwise, as seen in FIG. 3, against the force of the compression spring 31. Thereupon, as the hand lever 27 is thus disengaged by the locking lever 29, the movable gripping jaw 25 will pivot counterclockwise with the hand lever under the force of the tension spring 30 thereby gripping and so collapsing the inflow pipe 3 of the collection bag unit 1 between itself and the fixed gripping jaw 24. No more blood will now be admitted into the bag 2. The vacuum pump P, if it has been in operation, may also be set out of operation at the same time with the energization of the solenoid SOL. Further the vacuum chamber 6 may be placed in communication with the atmosphere as by opening an unshown solenoid valve.

Of course, for the accurate determination of the amount of blood collected, the sum of the weight of the weighing platform 21 and that of the bag unit 1 must be deducted from the gross weight exerted on the load cell L in order to obtain the net weight of the blood. The weight of the platform 21 is constant, so that its value may be previously input to the controller CT. However, the weight or so-called "tare" of the bag unit 1 is variable, depending upon its capacity and material and the amount of the anticoagulant prefilled therein, so that each bag unit must be weighed preparatory to the start of blood collection.

Another problem manifests itself in connection with the measurement of the variable tare, for the load cell is mounted on the swing cradle 11 oscillating about the horizontal pivot 8. Any load placed on the weighing platform 21 strains the load cell L to varying degrees depending upon its angular position. Accordingly, for the precise weighing of successive new bag units, the angular position of the load cell must be constant. The load cell is capable of most precise measurement when the weighing platform 21 and therefore the load cell itself are in a horizontal position. Moreover, the bag unit 1 can be easily placed centrally on the weighing platform 21 when the latter is horizontal. It is therefore desirable that the weighing platform be horizontal when each new bag unit is tared as just before the start of blood collection. However, the angular position of the weighing platform is indefinite at the end of each run of blood collection and, in consequence, must be readjusted before taring each new bag unit.

Figure 10:
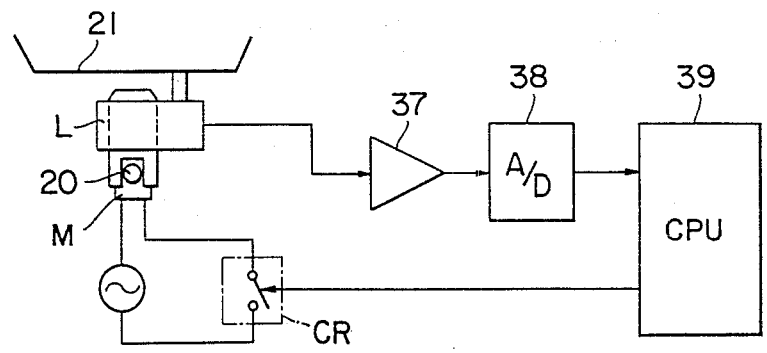
FIG. 10 is a block diagram of the electrical control system for use in obtaining the horizontal attitude of the weighing platform at the start of blood collection.
Figure 11:
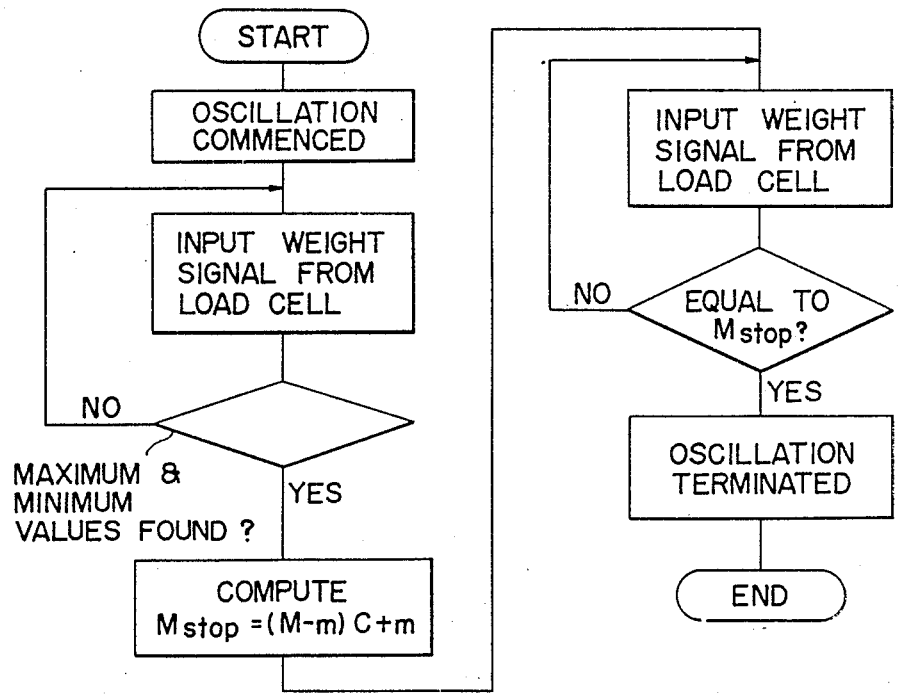
FIG. 11 is a flow chart explanatory of the operation of the control system of FIG. 10.

FIG. 10 block diagrammatically illustrates an example of means herein employed for automatic readjustment of the angular position of the load cell L as well as the weighing platform 21 in order to make them horizontal before taring each new bag unit. The load cell L is electrically coupled to a microprocessor or central processing unit (CPU) 39 via an operational amplifier 37 and analog-to-digital (A/D) converter 38. The CPU 39 has an output coupled to an on-off switch such as a solid-state relay CR connected in an alternating current supply circuit for the drive motor M which oscillates the load cell L via the eccentric cam 20. The following operational description of FIG. 10 will be better understood by referring to the flow chart of FIG. 11.

The CPU 39 is so programmed that, as the blood collection apparatus is electrically turned on, the switch CR is immediately closed to set the drive motor M into operation and hence to start oscillation of the weighing platform 21, with no bag unit loaded thereon. The load cell L will then put out the weight signal representative of the weight of the unloaded platform 21, which weight will vary with the oscillation of the platform and load cell. Inputting the digitized weight signal from the A/D converter 38, the microprocessor 39 is programmed to ascertain the maximum value M and minimum value m of the weight signal and further to compute the difference (M−m) therebetween.

Figure 9:
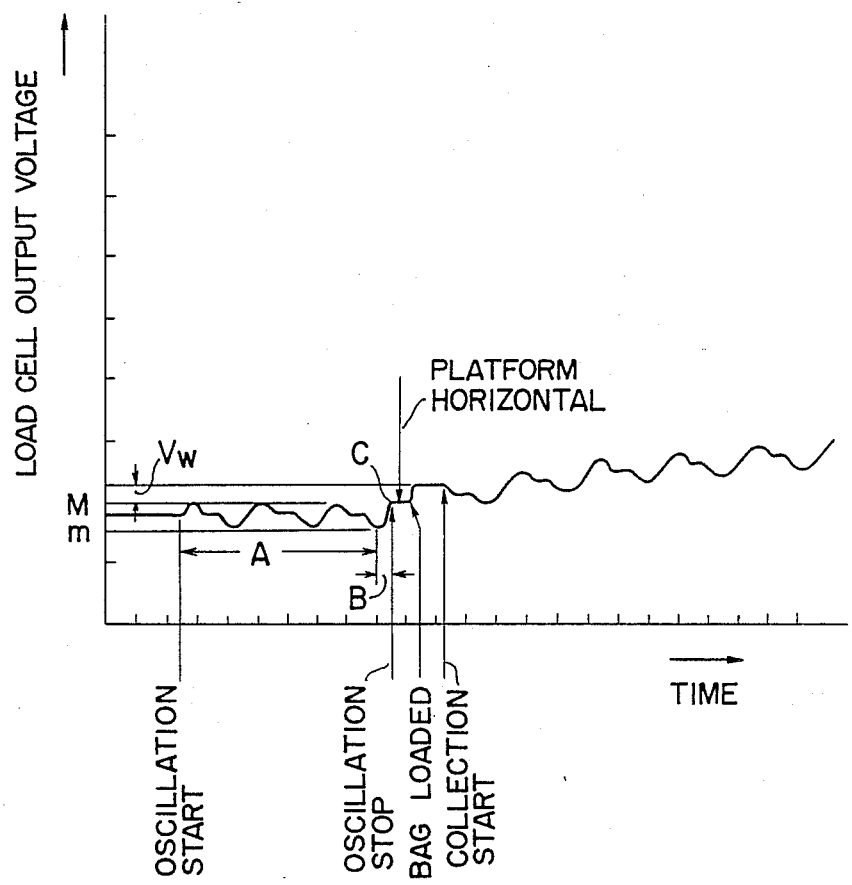
FIG. 9 is a graph plotting the output voltage of the load cell against time, the graph being explanatory of the way in which the shaking or oscillation of the weighing platform is terminated when it gains a horizontal attitude prior to blood collection.

As indicated at A in the graph of FIG. 9, the output voltage (weight signal) of the load cell L will vary cyclically between the maximum M and minimum m with the oscillation of the unloaded platform 21. The CPU 39 computes the difference between the maximum M and minimum m magnitudes of the weight signal incoming during at least one, preferably three, cycles of the weight signal. Then the CPU proceeds to compute the magnitude Mstop of the weight signal at which the oscillation of the weighing platform 21 is to be terminated, in accordance with the formula:

$$Mstop = (M - m)C + m$$

wherein C is a constant in the range of about 0.85–0.95, preferably about 0.90. In other words, the drive motor M is to be set out of rotation when the magnitude of the subsequently incoming weight signal becomes slightly less than the previously ascertained maximum value M.

Thus, as seen at B in FIG. 9, the oscillation of the unloaded platform 21 is continued after the initial three cycles of the weight signal during which its maximum and minimum values have been obtained. When, during the immediately following cycle, the magnitude of the weight signal increases and reaches the prescribed magnitude Mstop as at C in FIG. 9, the CPU will put out a signal for opening the on-off switch CR thereby terminating the oscillation of the unloaded platform 21.

It is to be noted that the drive motor M is set out of rotation not at the exact moment the weighing platform 21 gains the horizontal attitude but shortly before that moment. This is because the platform remains in motion by inertia for a brief period after the drive motor has been de-energized. It is therefore essential that the drive motor be set out of rotation while the weight signal from the load cell L is increasing in magnitude, that is, while the weighing platform is swinging toward, rather than away from, the horizontal position. Experiment has proved that the unloaded platform 21 stops approximatley in the horizontal position if the drive motor M is set out of rotation when the magnitude of the weight signal increases to about 85 to 95 per cent of the difference between the maximum M and minimum m values, depending, of course, upon such parameters as the weights of the load cell, weighing platform, etc., and the speed of oscillation.

Now that the weighing platform 21 has been stopped horizontally, a new collection bag unit 1 may be placed thereon. An inspection of FIG. 9 will show that the loading of the empty bag unit on the horizontal platform 21 results in an increase in the magnitude of the weight signal by Vw. This increase represents the tare to be deducted, at the CPU 39, from the subsequent weighing of the collected blood. The drive motor M is again set into rotation following the loading of the empty bag unit 1 on the weighing platform 21, and the blood is collected from the donor in the bag unit, as has been set forth previously. The collection can be terminated when the net weight of the collected blood (i.e. the gross weight minus the above obtained tare) reaches a preselected value.

Figure 12:
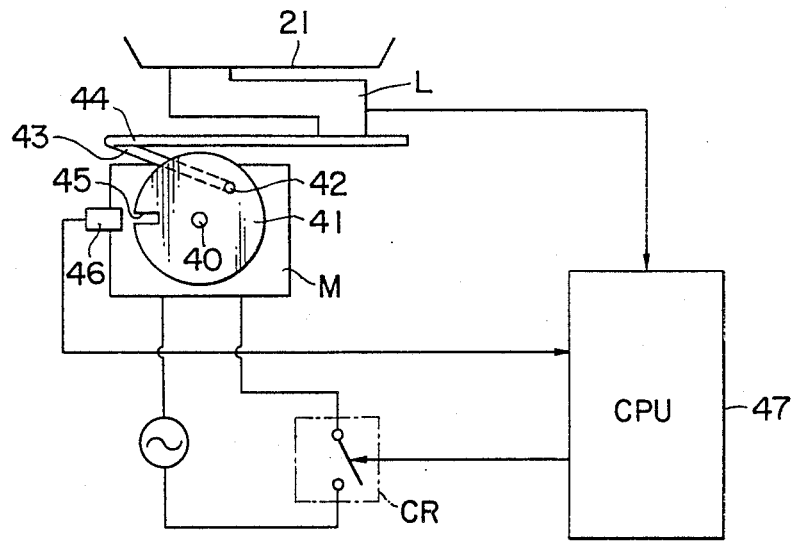
FIG. 12 is a diagrammatic illustration of an alternative system for obtaining the horizontal attitude of the weighing platform at the start of blood collection.

FIG. 12 is a diagrammatic illustration of another possible arrangement for gaining the horizontal attitude of the weighing platform 21 in order to tare each new bag unit preparatory to blood collection. The load cell L with the weighing platform 21 thereon is mounted on a swing cradle 44 capable of oscillation about a horizontal axis. In this embodiment, however, the swing cradle 44 is operatively coupled to one end of a link 43. The other end of this link is pivotally coupled at 42 to a rotary member such as a disk 41 in an eccentric position thereon. The disk 41 is mounted on the armature shaft 40 of a drive motor M for joint rotation therewith. Thus the rotation of the drive motor M is translated into the oscillation of the swing cradle 44.

Disposed in a prescribed position adjacent the periphery of the disk 41 is a photosensor 46 for optically sensing a slit 45 or like optically detectable mark formed on the disk 41 in an eccentric position thereon. The angular position of the slit 45 on the disk 41 is predetermined in relation to the fixed position of the photosensor 46 so that the latter detects the slit when the weighing platform 21 comes to the horizontal position. The photosensor 46 is connected to a CPU 47, which has an output coupled to an on-off switch CR connected in the alternating current supply circuit of the motor M.

Figure 13:
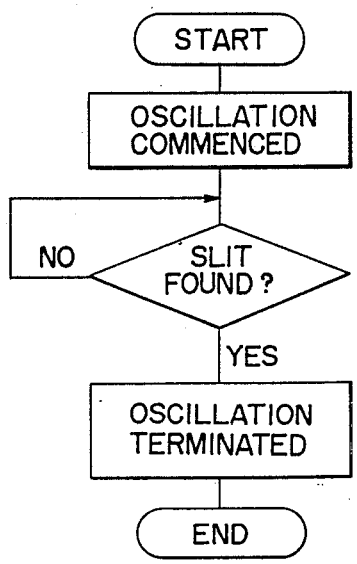
FIG. 13 is a flow chart explanatory of the operation of the system of FIG. 12.

The following operational description of FIG. 12 will be better understood by referring to the flow chart of FIG. 13 showing the sequential steps for obtaining the horizontal position of the weighing platform 21. As the drive motor M is set into rotation with the closure of the switch CR, the disk 41 will rotate to cause the oscillation of the unloaded weighing platform 21. When the platform subsequently comes to the horizontal position, the photosensor 46 will detect the slit 45 in the disk 41 and deliver its output to the CPU 47. Thereupon the CPU will respond by opening the switch CR to terminate the rotation of the drive motor M and, in consequence, the oscillation of the weighing platform 21 in the horizontal position. A new bag unit may now be loaded on the platform for taring prior to blood collection.

This alternative method offers the advantage that the weighing platform can be stopped in the horizontal position within one complete revolution of the drive motor, in contrast to the first described method which requires several revolutions of the drive motor. An additional advantage is that the platform can be stopped in a more precisely horizontal attitude by this second disclosed method than by the first.

What is claimed is:
1. A blood collection apparatus for use with a collection bag unit having an inflatable bag in which an anticoagulant is prefilled and which is to be filled with a preselected amount of blood, a collapsible inflow pipe extending from an communicating with the bag for introducing the blood therein, and a needle at the tip of the inflow pipe for blood collection from a donor, the apparatus comprising:
  (a) a weighing platform to be loaded with the bag of the collection bag unit during collection;
  (b) a load cell fixedly coupled to the bottom of the weighing platform for producing an electric weight signal representative of the weight of the blood being collected in the bag on the weighing platform;
  (c) a swing cradle having the load cell mounted thereto and being capable of joint oscillation with the load cell and the weighing platform about a fixed horizontal axis to cause the weighing platform to oscillate past a preassigned horizontal position;
  (d) shaking means acting on the swing cradle for oscillating the same about the horizontal axis and hence for shaking the bag on the weighing platform in order to intimately mingle the collected blood with the prefilled anticoagulant;
  (e) control means responsive to the weight signal from the load cell for producing a collection stop signal when the preselected amount of blood is collected in the bag;

(f) collection stop means responsive to the collection stop signal from the control means for terminating the blood collection by collapsing the inflow pipe of the collection; and (g) oscillation stop means for causing the shaking means to stop the oscillation of the swing cradle when the weighing platform is in said horizontal position, said oscillation stop means including processor means for ascertaining maximum and minimum values of the weight signal from the load cell during the oscillation of the swing cradle prior to the loading of the bag on the weighing platform and for stopping the oscillation of the swing cradle during the blood collection into the bag on the weighing platform immediately before the maximum value of the weight signal is reached.

2. The blood collection apparatus of claim 1 wherein the shaking means comprises:

(a) an electric drive motor having an output shaft; and (b) an eccentric cam mounted eccentrically on the output shaft of the drive motor for joint rotation therewith and acting on the swing cradle for oscillating the same about the horizontal axis.

3. The blood collection apparatus of claim 1 wherein the collection stop means comprises:

(a) a pair of gripping jaws movable toward and away from each other;

(b) resilient means biasing the gripping jaws toward each other;

(c) means for moving the gripping jaws away from each other against the bias of the resilient means;

(d) locking means engageable with the moving means for locking the gripping jaws away from each other against the bias of the resilient means; and (e) actuator means for acting on the locking means in response to the collection stop signal from the control means for unlocking the gripping jaws and permitting the same to move toward each other under the bias of the resilient means.

4. The blood collection apparatus of claim 1 further comprising:

(a) means defining a vacuum chamber for accommodating at least the weighing platform together with the bag loaded thereon; and (b) a vacuum pump for evacuating the vacuum chamber.

5. The blood collection apparatus of claim 1 wherein the shaking means comprises a drive motor, and the oscillation stop means comprises a switch for the on-off control of the drive motor, said processor means being electrically coupled to the load cell for inputting the weight signal therefrom, the processor means being also coupled to the switch for opening the same and hence for stopping the oscillation of the weighing platform.

6. A blood collection apparatus for use with a collection bag unit having an inflatable bag in which an anticoagulant is prefilled and which is to be filled with a preselected amount of blood, a collapsible inflow pipe extending from and communicating with the bag for introducing the blood therein, and a needle at the tip of the inflow pipe for blood collection from a donor, the apparatus comprising:

(a) a weighing platform to be loaded with the bag of the collection bag unit during blood collection;

(b) a load cell coupled to the weighing platform for producing an electric weight signal representative of the weight of the blood being collected in the bag on the weighing platform;

(c) a swing cradle having the load cell mounted thereto and being capable of joint oscillation with the load cell and the weighing platform about a fixed horizontal axis to cause the weighing platform to oscillate past a preassigned horizontal position;

(d) shaking means acting on the swing cradle for oscillating the same about the horizontal axis and hence for shaking the bag on the weighing platform in order to intimately mingle the collected blood with the prefilled anticoagulant, said shaking means comprising a drive motor and a rotary member capable of joint rotation therewith;

(e) control means responsive to the weight signal from the load cell for producing a collection stop signal when the preselected amount of blood is collected in the bag;

(f) collection stop means responsive to the collection stop signal from the control means for terminating the blood collection by collapsing the inflow pipe of the collection; and (g) oscillation stop means for causing the shaking means to stop the oscillation of the swing cradle when the weighing platform is in said horizontal position, preparatory to the loading of the bag thereon, said oscillation stop means comprising:

(i) a switch for the on-off control of the drive motor;

(ii) a photosensor capable of sensing a mark formed in a preassigned angular position on the rotary member when the weighing platform is in said horizontal position; and (iii) processor means electrically coupled to the switch and the photosensor for opening the switch and hence for stopping the oscillation of the weighing platform when the photosensor senses the mark on the rotary member.

7. A method of blood collection into a bag unit having a bag prefilled with an anticoagulant, which comprises:

(a) providing a load cell having a weighing platform coupled thereto, the load cell and the weighing platform being capable of joint oscillation about a fixed horizontal axis;

(b) oscillating the load cell and the weighing platform about the horizontal axis with no load placed on the weighing platform;

(c) stopping the oscillation of the load cell and the unloaded weighing platform when the latter comes to a horizontal position;

(d) taring the bag on the weighing platform in the horizontal position;

(e) collecting blood into the bag on the weighing platform with the latter maintained in constant oscillation with the load cell for intimately intermingling the collected blood and the anticoagulant; and (f) terminating the blood collection when a preselected amount of blood is collected as measured by the net weight of the blood within the bag;

wherein the oscillation of the load cell and the unloaded weighing platform is stopped by:

(a) ascertaining the maximum weight M and minimum weight m of the unloaded weighing platform from the output voltage of the load cell during the oscillation of the load cell and the unloaded weighing platform;

(b) computing the weight Mstop of the unloaded weighing platform at which the oscillation is to be stopped, in accordance with the equation:

$$M_{stop} + (M - m) C + m$$

where C is a constant in the range of about 0.85–0.95; and (c) stopping the oscillation when the actual weight of the unloaded weighing platform, as measured from the output voltage of the load cell, subsequently rises to the above computed value of Mstop.

8. The blood collection method of claim 7 wherein the oscillation of the load cell and the unloaded weighing platform is stopped by:

(a) oscillating the load cell and the unloaded weighing platform by a drive motor via a rotary member capable of joint rotation therewith; and (b) stopping the oscillation when a mark formed in a preassigned angular position on the rotary member is detected.

* * * * *